mber of the head portion. The anvil can be connected to the distal end of the connection member. The connection member can be configured to allow, along an axial direction, a portion thereof to be separated and ends of the remaining portion to be joined together.

(12) United States Patent
Yamakawa (10) Patent No.: US 8,845,662 B2
(45) Date of Patent: Sep. 30, 2014

(54) VASCULAR ANASTOMOSIS DEVICE

(75) Inventor: Kenji Yamakawa, Kanagawa (JP)

(73) Assignee: Fujifilm Corporation, Tokyo (JP)

(*) Notice: Subject to any disclaimer, the term of this patent is extended or adjusted under 35 U.S.C. 154(b) by 45 days.

(21) Appl. No.: 13/431,871

(22) Filed: Mar. 27, 2012

(65) Prior Publication Data

US 2012/0253367 A1 Oct. 4, 2012

(30) Foreign Application Priority Data

Mar. 29, 2011 (JP) ................... 2011-073117

(51) Int. Cl.
*A61B 17/08* (2006.01)

(52) U.S. Cl.
USPC ........................ 606/153; 227/175.1

(58) Field of Classification Search
USPC ............ 606/151–156, 213, 215, 219–221; 227/175.1–182.1

See application file for complete search history.

(56) References Cited

U.S. PATENT DOCUMENTS

| 5,395,030 | A  | * | 3/1995 | Kuramoto et al. | .......... | 227/179.1 |
| 6,338,737 | B1 | * | 1/2002 | Toledano | ...................... | 606/219 |
| 6,419,699 | B1 | * | 7/2002 | Schuessler | ................ | 623/11.11 |
| 2002/0161281 | A1 | * | 10/2002 | Jaffe et al. | ..................... | 600/114 |
| 2004/0167549 | A1 | * | 8/2004 | Boone et al. | ................. | 606/151 |

FOREIGN PATENT DOCUMENTS

JP 11-004832 A 1/1999

* cited by examiner

*Primary Examiner* — David Eastwood
(74) *Attorney, Agent, or Firm* — McGinn IP Law Group, PLLC (57) ABSTRACT

A vascular anastomosis device of an aspect of the presently disclosed subject matter can include: a head portion that is provided on a distal side of an insertion portion and is capable of projecting a joining member and a cutting member from a distal surface thereof; an anvil configured to deform the joining member projecting from the head portion at a position where the anvil faces the distal surface of the head portion; and a connection member that can be installed so as to be able to project from and retract into the head portion. The anvil can be connected to the distal end of the connection member. The connection member can be configured to allow, along an axial direction, a portion thereof to be separated and ends of the remaining portion to be joined together.

17 Claims, 8 Drawing Sheets

VASCULAR ANASTOMOSIS DEVICE

BACKGROUND OF THE INVENTION

1. Field of the Invention

The presently disclosed subject matter relates to a vascular anastomosis device. In particular, the presently disclosed subject matter relates to a vascular anastomosis device including a long insertion portion to be inserted into a lumen to anastomose lumen tissue.

2. Description of the Related Art

A vascular anastomosis device for anastomosing cut ends of an intestinal tract excised in a surgical operation (hereinafter sometimes referred to as "automatic anastomosis device") has been known (see, e.g., Japanese Patent Application Laid-Open No. 11-004832).

Generally, an automatic anastomosis device includes: an operating portion; a head portion that is provided at a distal end portion of an insertion portion which is connected to the operating portion and is inserted into a body cavity, and has a staple and a cutter therein; and an anvil positioned to face the head portion for deforming the staple.

After a lesion, such as cancer, is excised from the intestinal tract by a surgical operation, the anvil is inserted into one end of the intestinal tract from which the lesion is excised, and the cut end of the intestinal tract is tied around the anvil shaft extending from the anvil in a purse-string fashion so as to wrap the anvil. Meanwhile, the insertion portion is inserted from another incision site of the intestinal tract or is inserted via a transanal route, and tying in a purse-string fashion is performed while the center shaft extending from the head portion at the distal end of the insertion portion projects from another end.

After the completion of the purse-string suture of each intestinal tract end, with the center shaft being connected to the anvil shaft, the distance between the head portion and the anvil is reduced. And then, annularly arranged staples are projected toward the anvil and thus deformed. At the same time, unnecessary tissue inside the staple row is cut away by a cylindrical cutter. The anastomosis is thus completed.

SUMMARY OF THE INVENTION

However, according to a conventional automatic anastomosis device, the cut ends of the intestinal tract are sometimes left open in the abdominal cavity, leading to a problem of intra-abdominal contamination.

In order to solve this problem, Japanese Patent Application Laid-Open No. 11-004832 proposes the following method. For example, when an anastomosis is performed through an anus, an anvil is previously inserted from the anus beyond an affected area (lesion site) and indwelled in a position on a mouth side with respect to the excision site, and excision is performed with both the mouth and anus sides of the intestinal tract to be excised being closed using an automatic suture device. According to this method, the cut ends of the intestinal tract can be prevented from being left open in the abdominal cavity. However, the anvil has to be inserted prior to the insertion of the insertion portion into the intestinal tract. This complicates the operation. And, because of the prolonged operation time, an increased physical burden is placed on the patient.

It is desirable to provide a vascular anastomosis device that allows an anvil to be inserted into a lumen by a simple operation and also allows lumen tissue to be anastomosed without leaving cut lumen ends open in an abdominal cavity.

A vascular anastomosis device of an aspect of the presently disclosed subject matter, can insert a long insertion portion into the lumen to anastomose lumen tissue. The vascular anastomosis device of the aspect can include: a head portion that is provided on a distal side of the insertion portion and is capable of projecting a joining member and a cutting member from a distal surface thereof; an anvil configured to deform the joining member projecting from the head portion at a position where the anvil faces the distal surface of the head portion; and a connection member that can be installed so as to be able to project from and retract into the head portion. The anvil can be connected to the distal end of the connection member. The connection member can be configured to allow, along an axial direction, a portion thereof to be separated and ends of the remaining portion to be joined together.

According to the aspect, the insertion portion can be inserted via a transanal route or via an oral route into the lumen, and, with respect to the excision site in the lumen, the head portion is placed proximally, while the anvil is placed distally. In such a state, a purse-string suture can be performed around the connection member in such a manner to wrap each of the head portion and the anvil. Then, the excision site between the head portion and the anvil can be excised. A portion of the connection member corresponding to the excision site can be separated together with the excision site, while the ends of the remaining portion of the connection member can be joined together. As a result, the anvil can be inserted into the lumen by a simple operation. In addition, the cut ends of the lumen can be anastomosed without leaving the cut lumen ends open in the abdominal cavity. Therefore, it is possible to prevent intra-abdominal contamination.

The connection member can include a plurality of link members, and the link members are connectable to and separable from one another.

The link members connected to each other can be configured such that one link member is swingable within a predetermined angle range with respect to the other link member, and the connection member can be a bendable flexible shaft.

Of the link members that are adjacent to each other along the axial direction of the connection member, one link member can be provided with a fitting concave portion, while the other link member can be provided with a fitting convex portion that can be fitted into the concave portion. The link members can be connected to each other by fitting the fitting convex portion into the fitting concave portion.

The link members can be each provided with the fitting concave portion and the fitting convex portion.

Of the link members that are adjacent to each other along the axial direction of the connection member, one link member can be provided with a female screw, while the other link member can be provided with a male screw that can be screwed into the female screw. The link members can be connected to each other by screwing the male screw into the female screw.

The link members can be a plurality of annular members connected in a chain-like fashion.

The annular members can be each provided with a notch in a portion of the circumference thereof.

The annular members can each include: a substantially C-shaped body including an opening formed by a notch in a portion of the circumference thereof; and an opening-and-closing portion with one longitudinal end thereof being pivotally supported to open and close the opening.

The link members can be a plurality of S-shaped hook members connected in a chain-like fashion.

The connection member can have a convexoconcave pattern (an uneven pattern) formed in a lateral surface thereof along an axial direction.

The connection member can be a plate-like member that is long and narrow. The plate-like member can include a surface fastener formed on a surface thereof.

The connection member can have holes formed at a predetermined pitch along an axial direction. Separated ends of the connection member can be connected to each other using a connecting tool that can be inserted through the holes.

The connection member can be formed of a resin member. The separated ends of the connection member can be connected to each other by ultrasonic bonding or thermal bonding.

According to an aspect of the presently disclosed subject matter, the insertion portion can be inserted into the lumen via a transanal route or via an oral route, and, with respect to the excision site in the lumen, the head portion is placed proximally, while the anvil is placed distally. In such a state, a purse-string suture can be performed around the connection member in such a manner to wrap each of the head portion and the anvil. Then, the excision site between the head portion and the anvil can be excised. A portion of the connection member corresponding to the excision site can be separated together with the excision site, while the ends of the remaining portion of the connection member can be joined together. As a result, the anvil can be inserted into the lumen by a simple operation, and also, the cut ends of the lumen can be anastomosed without leaving the cut lumen ends open in the abdominal cavity. Therefore, it is possible to prevent intra-abdominal contamination.

DETAILED DESCRIPTION OF EXEMPLARY EMBODIMENTS

Hereinafter, exemplary embodiments of the presently disclosed subject matter will be described with reference to the attached drawings.

Figure 1:
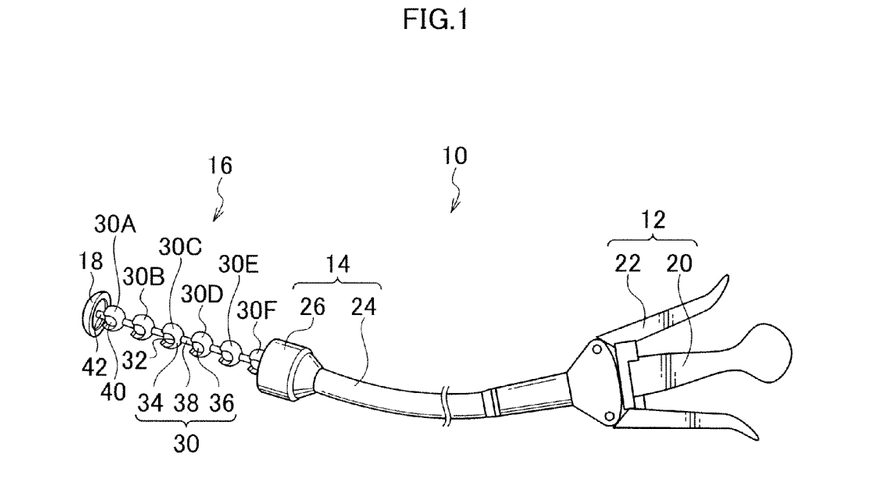
FIG. 1 is an external view illustrating an entire configuration of an automatic anastomosis device according to an embodiment of the presently disclosed subject matter.
Figure 2:
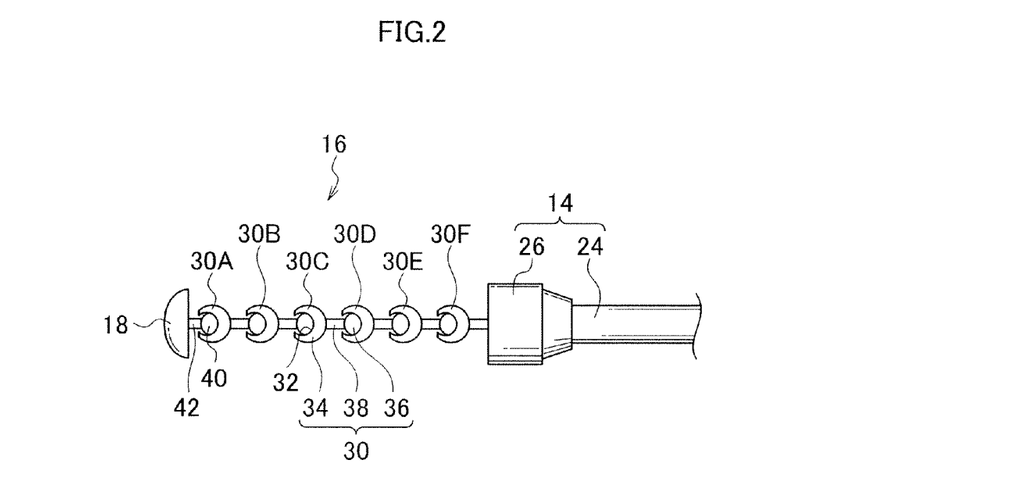
FIG. 2 is an enlarged side view of a portion of the automatic anastomosis device illustrated in FIG. 1.

FIG. 1 is an external view illustrating an entire configuration of an automatic anastomosis device according to an embodiment of the presently disclosed subject matter. FIG. 2 is an enlarged side view of a portion of the automatic anastomosis device illustrated in FIG. 1.

As illustrated in FIG. 1 and FIG. 2, an automatic anastomosis device 10 includes a operating portion 12, a head portion 26 that is provided at a distal end portion of an insertion portion 14 to be inserted into a body cavity and includes a staple and a cutter therein, an anvil 18 configured to deform the staple projecting from the head portion 26 at the position where the anvil 18 faces the head portion 26, and an anvil shaft 16 that can be installed so as to be able to project from and retract into the head portion 26 and can receive the anvil 18 connected to the distal end thereof (equivalent to "connection member" of the presently disclosed subject matter).

The operating portion 12 includes a rotary knob 20 configured to move the anvil 18 forward and backward via the anvil shaft 16, and a handle 22 configured to project the staple and the cutter (not illustrated) included in the head portion 26.

The insertion portion 14 includes a long flexible tube 24 which has sufficient flexibility to allow insertion into an examination site, and the head portion 26 which is provided at the distal end of the flexible tube 24. The proximal side of the anvil shaft 16 is inserted into the insertion portion 14 through a distal opening (not illustrated) formed in a distal surface of the head portion 26. The anvil shaft 16 moves forward and backward along a longitudinal direction of the insertion portion 14 in response to an operation of the rotary knob 20. In other words, the anvil shaft 16 is installed so as to be able to project from and retract into the head portion 26. Accordingly, the anvil 18 connected to the distal end of the anvil shaft 16 can move forward and backward with respect to the head portion 26. Then, the interval between the anvil 18 and the head portion 26 can be changed.

The anvil 18 has a flat disc-like shape and has substantially the same diameter as the head portion 26. Materials for the anvil 18 are not particularly limited. Preferred examples thereof include metals such as stainless steel and titanium, synthetic resins such as polyethylene terephthalate, polycarbonate, polystyrene, and polypropylene, and composite materials of these metals and synthetic resins.

The anvil shaft 16 is a connection member that can receive the anvil 18 connected to the distal end thereof. As mentioned above, the proximal side of the anvil shaft 16 is inserted into the insertion portion 14 through the distal opening of the head portion 26. The anvil shaft 16 can move forward and backward in response to the operation of the rotary knob 20. Then, the interval between the anvil 18 and the head portion 26 can be changed.

The anvil shaft 16 of this embodiment includes a plurality of top members 30 (equivalent to "link members" of the presently disclosed subject matter). The top members 30 are arranged in the axial direction of the anvil shaft 16 and connected to each other. The top members 30 all have the same configuration and are detachable from one another (i.e., connectable to and separable from one another).

The top members 30, 30 connected to each other along the axial direction of the anvil shaft 16 are configured such that one top member 30 is swingable within a predetermined angle range with respect to the other top member 30. That is, the anvil shaft 16 is a flexible shaft that can be turned in any direction (i.e., bendable). Thus, it is possible to insert the anvil shaft 16 deep into the lumen.

Hereinafter, the top members 30 forming the anvil shaft 6 will be described in detail.

As illustrated in FIG. 1 and FIG. 2, a top member 30 is an integrally molded body made of an elastically deformable metal or synthetic resin. The top member 30 includes a large spherical body 34 provided with a fitting concave portion 32, a small spherical body (fitting convex portion) 36 that can be fitted into the fitting concave portion 32, and a shaft member 38 that connects the large spherical body 34 and the small spherical body 36. Materials for such a top member 30 are not limited as long as they are elastically deformable. Preferred examples thereof include metals such as aluminum and stainless steel and synthetic resins such as polyurethane and polystyrene.

The large spherical body 34 has formed therein a fitting concave portion 32 corresponding to the shape of the small spherical body 36. The fitting concave portion 32 is open toward a lateral surface of the large spherical body 34 (in the direction perpendicular to the axial direction of the shaft member 38). This opening (side opening) serves as an insertion hole for inserting the small spherical body 36 into the fitting concave portion 32 and is configured such that the small spherical body 36 can be inserted therethrough. It is preferable that the side opening has a diameter that is slightly smaller than the diameter of the small spherical body 36. When the small spherical body 36 is pressed into the side opening with a predetermined force, the large spherical body 34 is elastically deformed, whereby the side opening is pushed and expanded. As a result, the small spherical body 36 can be fitted into the fitting concave portion 32. Further, the small spherical body 36 fitted into the fitting concave portion 32 cannot pass through the side opening unless a predetermined force is applied. Therefore, the fitting state between the small spherical body 36 and the fitting concave portion is not easily canceled.

The fitting concave portion 32 is open toward a front of the large spherical body 34 (in the axial direction of the shaft member 38, which is opposite to the side where the shaft member 38 is connected). This opening (front opening) is continuous to the side opening, and serves as an insertion hole for inserting therethrough the shaft member 38 connected to the small spherical body 36 fitted into the fitting concave portion 32. The front opening has a diameter larger than a diameter of the shaft member 38 and smaller than a diameter of the small spherical body 36. Thus, even under a pulling force applied to the anvil shaft 16 during a normal operation, the small spherical body 36 abuts against an inner wall surface of the large spherical body 34 and cannot pass through the front opening.

Incidentally, the size of the front opening is not particularly limited as long as only the shaft member 38 can be inserted therethough. However, it is preferable that the front opening has a sufficiently large diameter so as to ensure a predetermined space between an edge of the front opening and the shaft member 38, and so as not to allow the small spherical body 36 to pass therethough. As a result, of the top members 30, 30 connected to each other, one top member 30 is swingable within a predetermined angle range with respect to the other top member 30, and the anvil shaft 16 can be turned in any direction.

Further, the anvil shaft 16 includes a shaft member 42 and a small spherical body (fitting convex portion) 40. The shaft member 42 extends from a central part of the anvil 18 toward the proximal side (anvil-shaft-16 side). The small spherical body 40 can be connected to the proximal side of the shaft member 42 and can be fitted into the fitting concave portion 32 of the top member 30. The small spherical body 40 and the shaft member 42 have substantially the same configuration (i.e., substantially the same shape and size) as the small spherical body 36 and shaft member 38 of the top member 30, respectively. Therefore, as in the case where the top members 30, 30 are connected to each other, the top member 30 and the anvil 18 can be connected by fitting the small spherical body 40 of the anvil 18 into the fitting concave portion 32 of the top member 30.

Figure 3:
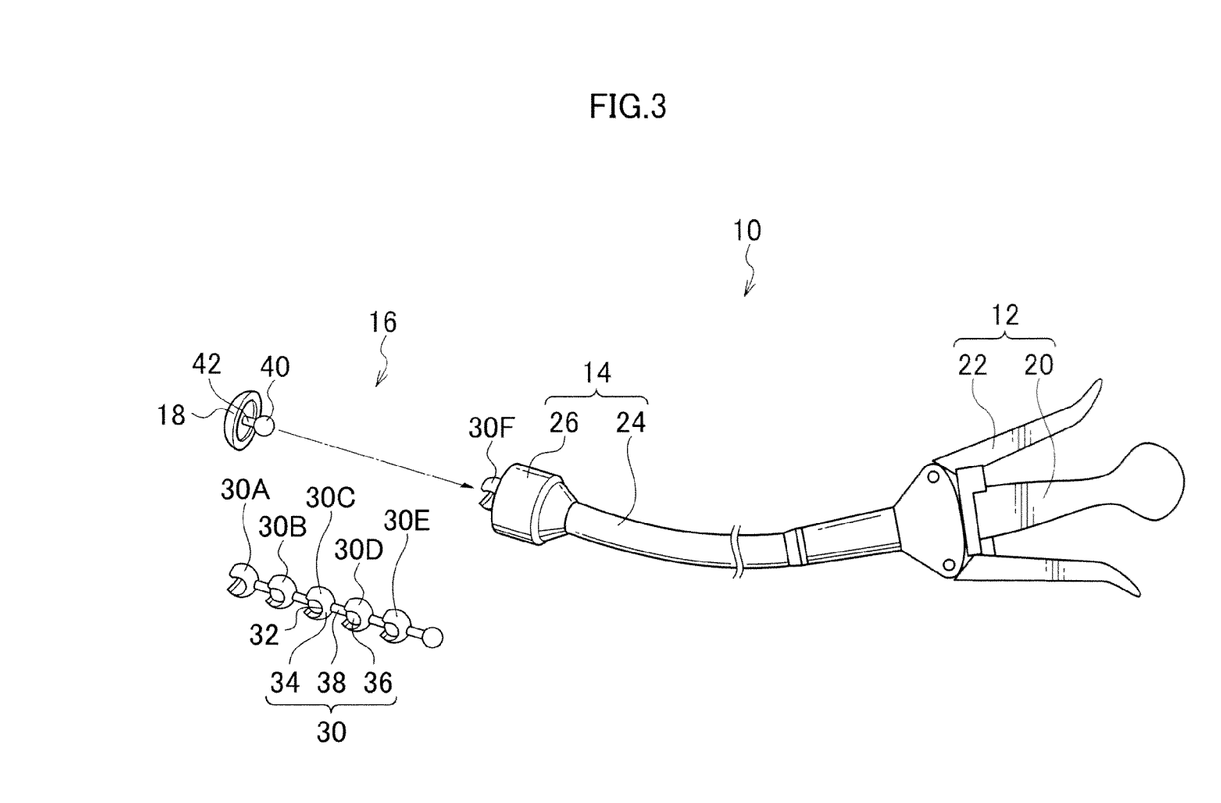
FIG. 3 is an external view illustrating a separation of a portion of a shaft.

As seen above, in this embodiment, the anvil shaft 16 includes a plurality of top members 30 that are detachable from one another. Accordingly, a portion of the anvil shaft 16 can be separated. And, the ends of the remaining portion can be joined together. As a result, for example, as illustrated in FIG. 3, of a plurality of top members 30A to 30F, some top members 30A to 30E can be separated. Further, by fitting the small spherical body 40, which can be connected to the anvil 18 via the shaft member 42, into the fitting concave portion 32 of the top member 30F, the ends of the remaining portion of the anvil shaft 16 can be connected to each other.

Although FIGS. 1 to 3 illustrate the structure in which six top members 30A to 30F are connected, the number of top members 30 forming the anvil shaft 16 is not particularly limited.

Next, the method for operating the automatic anastomosis device 10 of this embodiment will be described. FIGS. 4A to 4F are explanatory views illustrating an example of the method for operating the automatic anastomosis device 10. The following will describe the case where the insertion portion 14 is inserted via a transanal route to perform an anastomosis, but the same applies to the case where the insertion portion 14 is inserted via an oral route to perform an anastomosis.

Figure 4A:
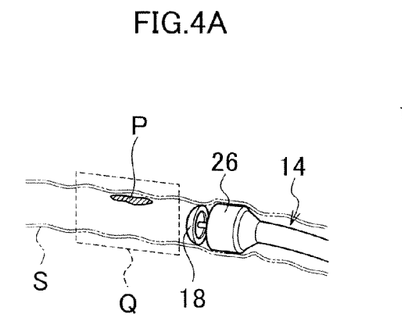
FIGS. 4A to 4F are explanatory views illustrating an example of operating procedure for the automatic anastomosis device.

First, as illustrated in FIG. 4A, the insertion portion 14 is inserted through the patient's anus into the intestinal tract S. At this time, the anvil 18 is connected to the distal end of the anvil shaft 16. The anvil shaft 16 is pulled into the insertion portion 14, and the insertion operation is performed with the anvil 18 being located close to the head portion 26. Then, when the head portion 26 is located proximal with respect to the excision site Q including the lesion site P (proximal side), the insertion operation is stopped.

Figure 4B:
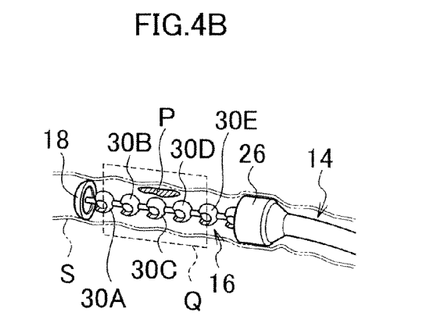

Next, the rotary knob 20 is rotated to let out the anvil shaft 16 from the head portion 26 of the insertion portion 14 as illustrated in FIG. 4B. Then, the anvil 18 connected to the distal end of the anvil shaft 16 is placed distal with respect to the excision site Q (distal side).

Figure 4C:
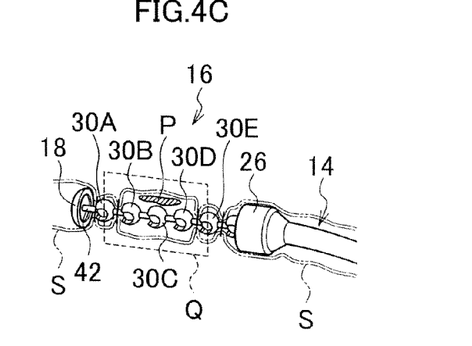

Next, as illustrated in FIG. 4C, the intestinal tract S is tied around the anvil shaft 16 (specifically the shaft member 42 or 38) in a purse-string fashion so as to wrap each of the anvil 18 and the head portion 26. At this time, it is preferable that the intestinal tract S is also tied in a position slightly inside with respect to each end of the excision site around the anvil shaft 16 in a purse-string fashion such that the lesion site P is included inside.

Figure 4D:
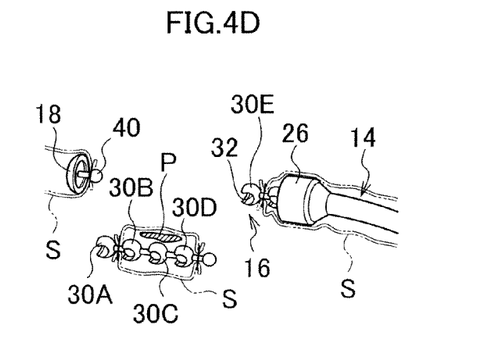

After the intestinal tract S is tied in at least two positions (preferably four positions) around the anvil shaft 16 in a purse-string fashion and thus closed, the intestinal tract S is cut in such a manner that the excision site Q is separated from the distal side (anvil-18 side) and proximal side (head-portion-26 side) of the intestinal tract S. At this time, the distal side (anvil-18 side) and proximal side (head-portion-26 side) of the intestinal tract S are closed. Therefore, the cut ends of the intestinal tract S are not left open in the abdominal cavity. Further, both ends of the excision site Q are closed such that the lesion site P is included inside. Therefore, the lesion site P can be prevented from being exposed in the abdominal cavity. Then, as illustrated in FIG. 4D, a portion of the anvil shaft 16 (top members 30A to 30D) and the excision site Q are integrally separated and recovered.

Figure 4E:
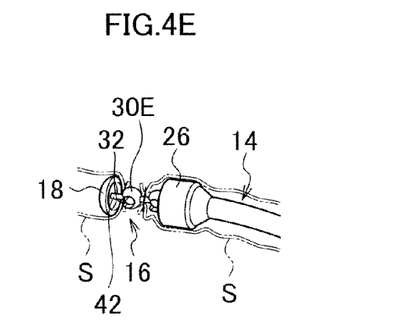

Next, as illustrated in FIG. 4E, the ends of the remaining portion of the anvil shaft 16 are joined together. In this example, the ends of the separated anvil shaft 16 are joined together by fitting the small spherical body 40 connected to the anvil 18 via the shaft member 42 into the fitting concave portion 32 of the sixth top member 30F.

Figure 4F:
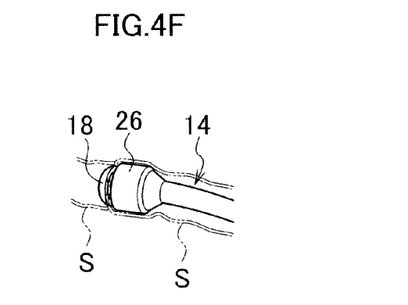

Then, the rotary knob 20 is rotated to pull the anvil shaft 16 into the insertion portion 14 as illustrated in FIG. 4F. The head portion 26 of the insertion portion 14 and the anvil 18 are brought close together and pressed against each other. At this time, the head portion 26 and the anvil 18 have therebetween the intestinal walls of both ends of the separated intestinal tract S. Then, the handle 22 is gripped, whereby a plurality of staplers are annularly driven from the head portion 26 across each end of the excised intestinal tract S. At the same time, the unnecessary intestinal wall portion inside the staplers is cut by a cylindrical cutter. The anastomosis of the cut ends of the intestinal tract S is thus completed.

As described above, according to this embodiment, the insertion portion 14 is inserted into the intestinal tract S through the anus, and the head portion 26 is placed proximally with respect to the excision site Q in the intestinal tract S, while the anvil 18 is placed distally with respect to the excision site Q in the intestinal tract S. In such a state, a purse-string suture is performed around the anvil shaft 16 in such a manner to wrap each of the head portion 26 and the anvil 18. Then, the excision site Q between the head portion 26 and the anvil 18 is excised. The portion of the anvil shaft 16 corresponding to the excision site Q is separated, while the ends of the remaining portion of the anvil shaft 16 are joined together. As a result, the cut ends of the intestinal tract S can be anastomosed without leaving the cut ends of the intestinal tract S open in the abdominal cavity. Therefore, intra-abdominal contamination can be prevented.

Further, since the anvil shaft 16 is formed of a flexible shaft that can be turned in any direction, the anvil 18 can be easily placed deep in the lumen (e.g., around the transverse colon, ascending colon, cecum, etc.).

Variations of the anvil shaft 16 of this embodiment (first to ninth variations) are illustrated in FIGS. 5 to 13. In FIGS. 5 to 13, common or similar components to FIG. 1 are indicated by the same reference numerals, and explanations are omitted.

Figure 5:
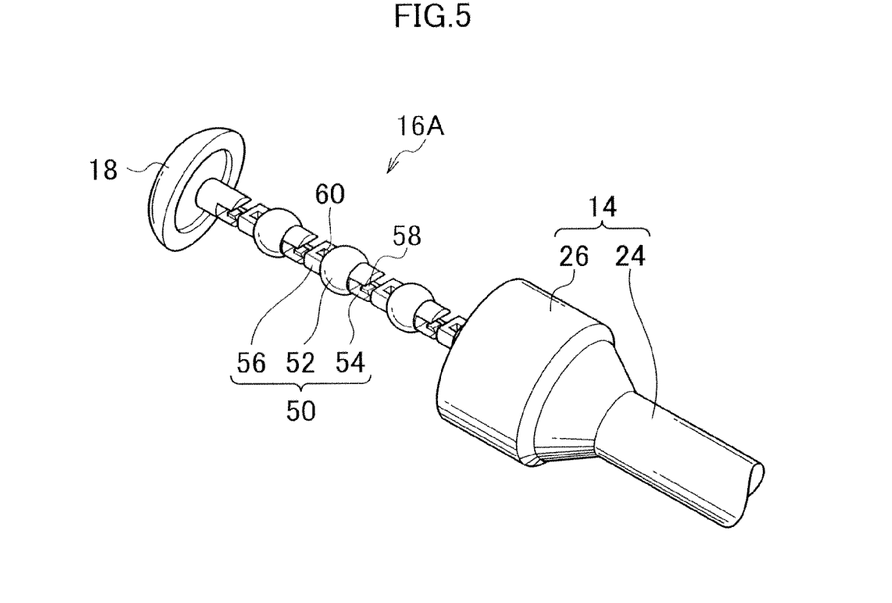
FIG. 5 is a schematic diagram illustrating a configuration of a shaft according to a first variation.

An anvil shaft 16A of the first variation illustrated in FIG. 5 has a structure in which a plurality of top members 50 are connected to each other. Each top member 50 includes a clip-like elastic latch piece 54 provided at one end of a spherical body portion 52. The elastic latch piece 54 includes inside an engaging convex portion 58 in a form of a protrusion. Meanwhile, the body portion 52 includes an elastic arm 56 that is provided at the other end thereof and can be inserted through the elastic latch piece 54. The elastic arm 56 includes an engaging concave portion 60 that can be engaged with the engaging convex portion 58. Then, when the elastic latch piece 54 of one top member 50 receives the elastic arm 56 of the other top member 50 inserted thereinto, the elastic latch piece 54 is elastically deformed to engage the engaging convex portion 58 of the one top member 50 with the engaging concave portion 60 of the other top member 50, whereby two top members 50, 50 are connected to each other. When a predetermined force or a force greater than the predetermined force is applied thereto in the longitudinal direction of the anvil shaft 16A, the engagement between the engaging convex portion 58 of the one top member 50 and the engaging concave portion 60 of the other top member 50 is canceled, whereby the two top members 50, 50 can be separated.

Figure 6:
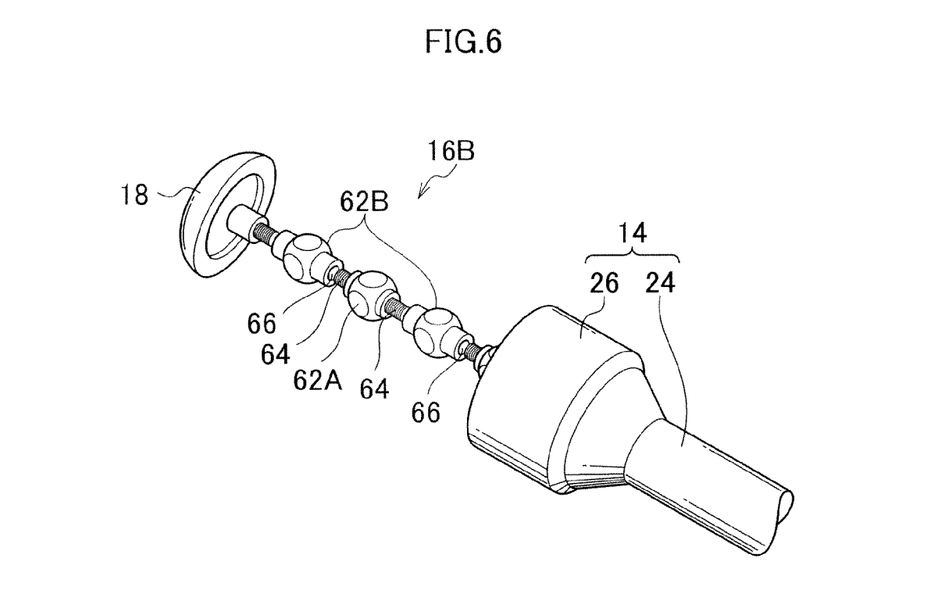
FIG. 6 is a schematic diagram illustrating a configuration of a shaft according to a second variation.

In an anvil shaft 16B of the second variation illustrated in FIG. 6, a first top member 62A having male screws 64, 64 at opposite ends thereof and a second top member 62B having female screws 66, 66 at opposite ends thereof are alternately placed along the axial direction of the anvil shaft 16B. By screwing the male screw 64 of the first top member 62A into the female screw 66 of the second top member 62B, the two top members 62A and 62B are connected to each other. Further, by unscrewing the male screw 64 from the female screw 66, the two top members 62A and 62B can be easily separated.

Incidentally, although the second variation illustrates a structure in which the anvil shaft 16B includes two kinds of top members 62A and 62B, the structure is not limited thereto. For example, when a top member having a male screw at one end thereof and a female screw at the other end is used, the commonality of top members forming an anvil shaft can be achieved, allowing for cost reduction.

Figure 7:
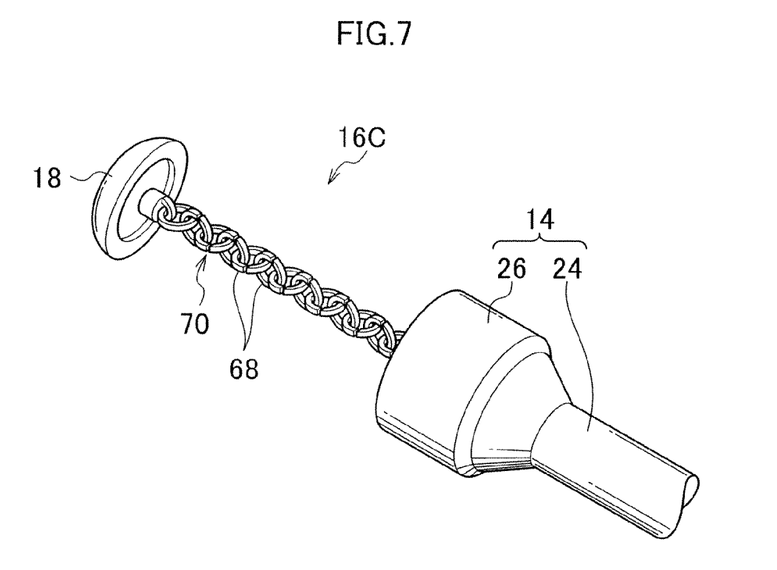
FIG. 7 is a schematic diagram illustrating a configuration of a shaft according to a third variation.

A shaft 16C of the third variation illustrated in FIG. 7 includes a plurality of annular members 68 connected in a chain-like fashion. Each annular member 68 has an opening 70 formed by a notch in the circumference thereof. The annular members 68, 68 are connected to and separated from each other through such openings 70.

Figure 8:
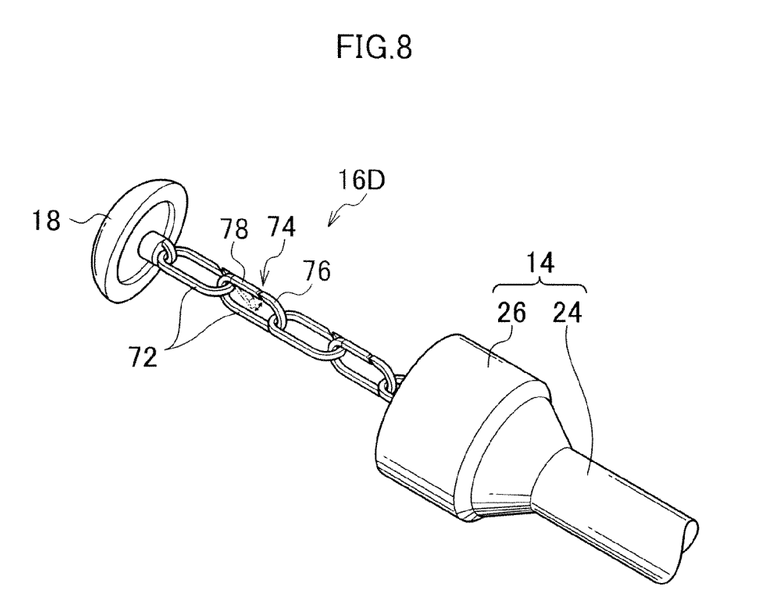
FIG. 8 is a schematic diagram illustrating a configuration of a shaft according to a fourth variation.

Similarly to the third variation, a shaft 16D of the fourth variation illustrated in FIG. 8 includes a plurality of annular members 72 connected in a chain-like fashion. The annular member 72 is formed like a carabiner. The annular member 72 includes a substantially C-shaped body 76, which has an opening 74 formed by a notch in a portion of the circumference thereof, and an opening-and-closing portion 78, whose one longitudinal end is pivotally supported to open and close the opening 74. The annular members 72 of this variation each have the opening-and-closing portion 78. Therefore, the annular members 72, 72 can be easily connected to and separated from each other.

Figure 9:
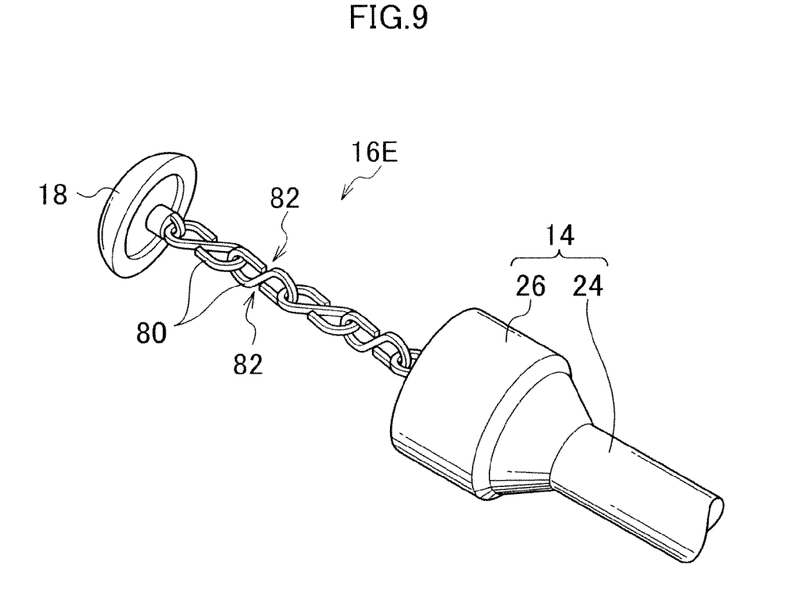
FIG. 9 is a schematic diagram illustrating a configuration of a shaft according to a fifth variation.

The shaft 16E of the fifth variation illustrated in FIG. 9 includes a plurality of S-shaped hook members (S-shaped hooks) 80 connected in a chain-like fashion. Each S-shaped hook member 80 has a space 82 created at each end of the S-shape. The S-shaped hook members 80, 80 can be easily connected to and separated from each other through such a space 82.

Figure 10:
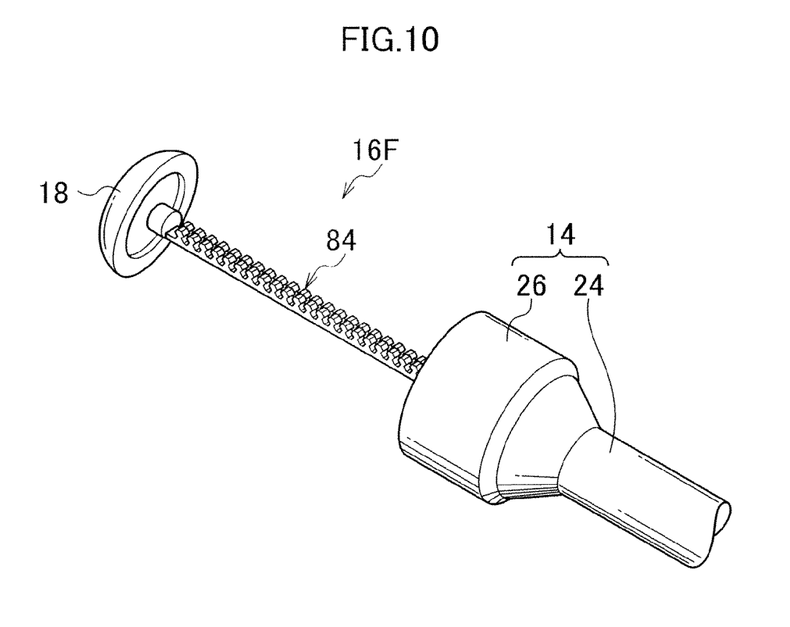
FIG. 10 is a schematic diagram illustrating a configuration of a shaft according to a sixth variation.

A shaft 16F of the sixth variation illustrated in FIG. 10 has a predetermined convexoconcave pattern 84 formed in a lateral surface thereof along an axial direction. The shaft 16F is formed of a member that can be cut at any positions (e.g., resin member). Cut ends of the cut shaft 16F can be connected to each other by placing the convexoconcave patterns 84 of such cut ends to face each other and engaging them together.

Figure 11:
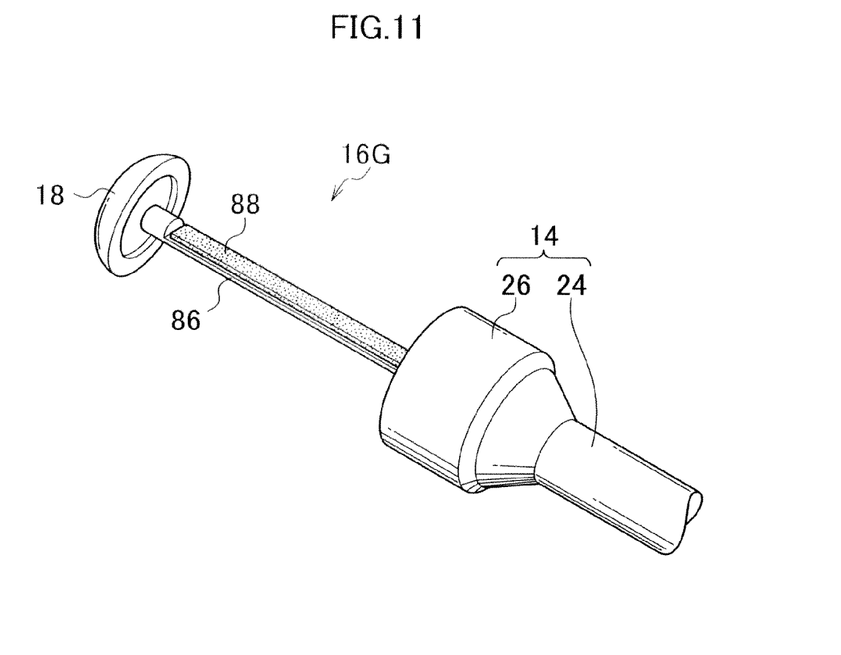
FIG. 11 is a schematic diagram illustrating a configuration of a shaft according to a seventh variation.

A shaft 16G of the seventh variation illustrated in FIG. 11 includes a plate-like member 86 that is long and narrow. The plate-like member 86 has a surface fastener 88 formed on the surface thereof. The shaft 16G is formed of a member that can be cut at any positions (e.g., resin member). The cut ends of the cut shaft 16G can be joined together via the surface fasteners 88 of such cut ends.

Figure 12:
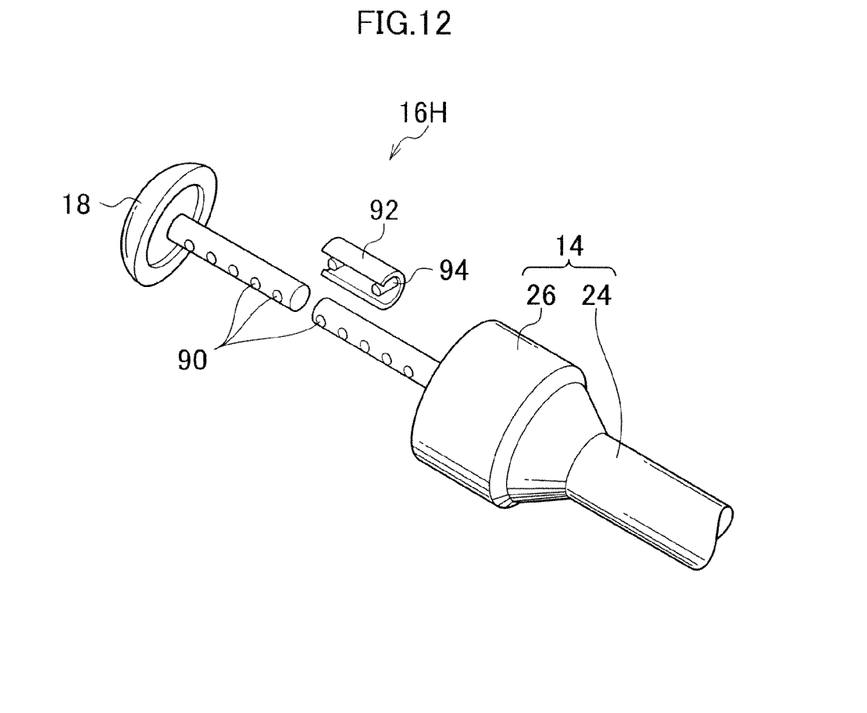
FIG. 12 is a schematic diagram illustrating a configuration of a shaft according to an eighth variation.

A shaft 16H of the eighth variation illustrated in FIG. 12 has holes 90 therethrough in the radial direction. The holes 90 are arranged at a constant pitch along an axial direction of the shaft 16H. The shaft 16H is formed of a member that can be cut at any positions (e.g., resin member). When cut ends of the cut shaft 16H are to be connected to each other, as illustrated in FIG. 12, the connection is made using an adapter member 92 having a C-shaped cross-section. The adapter member 92 has, on an inner surface thereof, pin members 94 that can be inserted through the hole 90. By inserting the pin member 94 of the adapter member 92 into the hole 90 of each cut end of the cut shaft 16H, the cut ends can be joined together. Instead of using the adapter member 92, the holes 90, 90 of the cut ends of the cut shaft 16H may also be threaded together.

Figure 13:
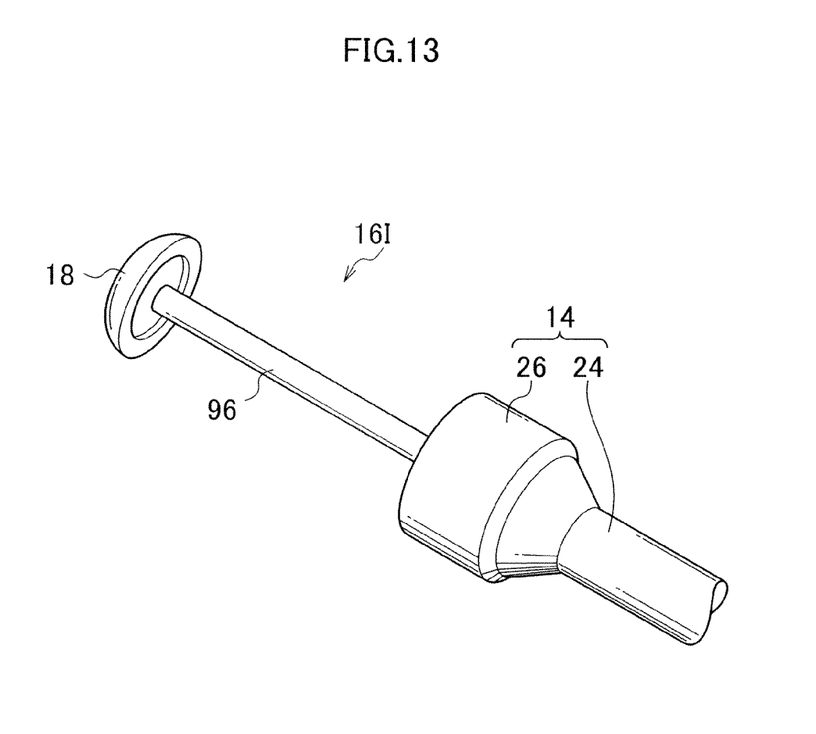
FIG. 13 is a schematic diagram illustrating a configuration of a shaft according to a ninth variation.

The shaft 16I of the ninth variation illustrated in FIG. 13 includes a rod-like member 96 formed of a resin member. The rod-like member 96 can be separated by cutting at any positions. The cut ends of the cut shaft 16I can be connected to each other by ultrasonic bonding or thermal bonding.

Thus, the shafts 16A to 16I respectively illustrated in FIGS. 5 to 13 are each configured to allow, in an axial direction, a portion thereof to be separated and the ends of the remaining portion to be joined together. Therefore, in the automatic anastomosis device 10 of this embodiment, it is possible to use these shafts 16A to 16I.

The vascular anastomosis device of the presently disclosed subject matter has been described above in detail. However, the presently disclosed subject matter is not limited to the above examples, and, needless to say, various improvements and modifications can be made without departing from the gist of the presently disclosed subject matter.

What is claimed is:

1. A vascular anastomosis device including an insertion portion configured for insertion into a lumen to anastomose lumen tissue, the vascular anastomosis device comprising:
   a head portion that is provided on a distal side of the insertion portion and is capable of projecting a joining member and a cutting member from a distal surface thereof;
   an anvil configured to deform the joining member projecting from the head portion at a position where the anvil faces the distal surface of the head portion; and
   a connection member comprising a plurality of connection member portions that can be installed so as to be able to project from and retract into the head portion, the anvil connected to a distal end of the connection member, the plurality of connection member portions being configured to allow a portion of the plurality of connection member portions projected from the distal end of the head portion to be separated and removed and ends of the remaining portions configured to be joined together.

2. The vascular anastomosis device according to claim 1, wherein
   the plurality of connection member portions are a plurality of link members, and
   the link members are connectable to and separable from one another.

3. The vascular anastomosis device according to claim 2, wherein
   the link members connected to each other are configured such that one link member is swingable within a predetermined angle range with respect to the other link member, and
   the connection member comprises a bendable flexible shaft.

4. The vascular anastomosis device according to claim 2, wherein
   a first link member of the link members that are adjacent to each other along the axial direction of the connection member includes a fitting concave portion,
   a second link member of the link members includes a fitting convex portion that can be fitted into the fitting concave portion, and
   the link members are connected to each other by fitting the fitting convex portion into the fitting concave portion.

5. The vascular anastomosis device according to claim 4, wherein
   the link members each include the fitting concave portion and the fitting convex portion.

6. The vascular anastomosis device according to claim 2, wherein
   a first link member of the link members that are adjacent to each other along the axial direction of the connection member is provided with a female screw,
   a second link member of the link members is provided with a male screw that can be screwed into the female screw, and
   the link members are connected to each other by screwing the male screw into the female screw.

7. The vascular anastomosis device according to claim 2, wherein
   the link members comprise a plurality of annular members connected in a chain-like fashion.

8. The vascular anastomosis device according to claim 7, wherein
   the annular members are each provided with a notch in a portion of the circumference thereof.

9. The vascular anastomosis device according to claim 7, wherein
   the annular members each include:
   a substantially C-shaped body having an opening formed by a notch in a portion of the circumference thereof; and
   an opening-and-closing portion with one longitudinal end thereof being pivotally supported to open and close the opening.

10. The vascular anastomosis device according to claim 2, wherein
    the link members comprise a plurality of S-shaped hook members connected in a chain-like fashion.

11. The vascular anastomosis device according to claim 1, wherein
    the connection member has a convexoconcave pattern formed in a lateral surface thereof along the axial direction.

12. The vascular anastomosis device according to claim 1, wherein
    the connection member includes a plate-like member defining the plurality of connection member portions, and
    the plate-like member has a surface fastener formed on a surface thereof.

13. The vascular anastomosis device according to claim 1, wherein
    the plurality of connection member portions have holes formed at a predetermined pitch along an axial direction, and
    separated ends of the plurality of connection member portions are connected to each other using a connecting tool that can be inserted through the holes.

14. The vascular anastomosis device according to claim 1, wherein
    the connection member is formed of a resin member defining the plurality of connection member portions, and
    separated ends of the plurality of connection member portions are connected to each other by ultrasonic bonding or thermal bonding.

15. The vascular anastomosis device according to claim 1, wherein the anvil has a flat disc shape, and
    wherein the anvil has a diameter substantially equal to a diameter of the head portion.

16. The vascular anastomosis device according to claim 2, wherein each link member of the plurality of link members is integrally formed.

17. The vascular anastomosis device according to claim 2, wherein a link member of the plurality of link members comprises:

a first spherical body that includes a fitting concave portion;
a second spherical body that is smaller than the first spherical body, the second spherical body includes a fitting convex portion that can be fitted into the fitting concave portion; and
a shaft member that connects the first spherical body to the second spherical body.

\* \* \* \* \*